(12) United States Patent
Aoshima et al.

(10) Patent No.: US 10,265,021 B2
(45) Date of Patent: Apr. 23, 2019

(54) BIOLOGICAL INFORMATION PROCESSING DEVICE, PROGRAM, AND BIOLOGICAL INFORMATION PROCESSING METHOD

(71) Applicant: SEIKO EPSON CORPORATION, Tokyo (JP)

(72) Inventors: Ichiro Aoshima, Matsumoto (JP); Fumio Koyama, Hara-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/608,413

(22) Filed: May 30, 2017

(65) Prior Publication Data

US 2017/0360368 A1 Dec. 21, 2017

(30) Foreign Application Priority Data

Jun. 17, 2016 (JP) ................. 2016-120474

(51) Int. Cl.
*A61B 5/00* (2006.01)
*A61B 5/11* (2006.01)
*A63B 24/00* (2006.01)
*G09B 19/00* (2006.01)
*A61B 5/024* (2006.01)

(52) U.S. Cl.
CPC ............ *A61B 5/681* (2013.01); *A61B 5/1118* (2013.01); *A61B 5/721* (2013.01); *A63B 24/0062* (2013.01); *G09B 19/0038* (2013.01); *A61B 5/0004* (2013.01); *A61B 5/02438* (2013.01); *A61B 5/7235* (2013.01); *A61B 5/7257* (2013.01); *A61B 5/7278* (2013.01)

(58) Field of Classification Search
CPC ....... A61B 5/681; A61B 5/721; A61B 5/1118; A61B 5/02438; A61B 5/7278; A61B 5/0004; A61B 5/7235; A61B 5/7257; A63B 24/0062; G09B 19/0038
See application file for complete search history.

(56) References Cited

U.S. PATENT DOCUMENTS

| | | | |
|---|---|---|---|
| 2012/0283525 A1 | 11/2012 | Kuroda | |
| 2016/0007935 A1* | 1/2016 | Hernandez | A61B 5/7278 600/301 |
| 2016/0081630 A1 | 3/2016 | Aoshima | |

FOREIGN PATENT DOCUMENTS

| | | |
|---|---|---|
| JP | 2012-232010 A | 11/2012 |
| JP | 2014-236775 A | 12/2014 |
| JP | 2015-157128 A | 9/2015 |

* cited by examiner

*Primary Examiner* — Scott M. Getzow
(74) *Attorney, Agent, or Firm* — Oliff PLC

(57) ABSTRACT

A biological information processing device includes: a pulse wave sensor which measures a pulse wave of a user; a body motion sensor which detects a body motion of the user; and a processing unit which performs estimation processing for pulse wave information of the user. The processing unit performs the estimation processing based on body motion information acquired using a signal from the body motion sensor, even if the pulse wave sensor is off.

20 Claims, 14 Drawing Sheets

| VELOCITY | PULSE RATE |
|---|---|
| $v_0 \sim v_1$ | $hr_0 \sim hr_1$ |
| $v_1 \sim v_2$ | $hr_1 \sim hr_2$ |
| $v_2 \sim v_3$ | $hr_2 \sim hr_3$ |
| $v_3 \sim v_4$ | $hr_3 \sim hr_4$ |

| MODE | FREQUENCY OF MEASUREMENT | TIMING OF ESTIMATION PROCESSING |
|---|---|---|
| EXERCISE MODE | ONCE EVERY SECOND | ONLY AT START OF EXERCISE |
| EVERYDAY-LIFE MODE | ONCE EVERY MINUTE | 5 SECONDS BEFORE MEASUREMENT STARTS |
| REST MODE | ONCE EVERY 10 MINUTES | 5 SECONDS BEFORE MEASUREMENT STARTS |
| SLEEP MODE | ONCE EVERY 5 MINUTES | 5 SECONDS BEFORE MEASUREMENT STARTS |
| MENTAL MEASUREMENT MODE | ONCE EVERY MINUTE | 5 SECONDS BEFORE MEASUREMENT STARTS |

FIG. 19

BIOLOGICAL INFORMATION PROCESSING DEVICE, PROGRAM, AND BIOLOGICAL INFORMATION PROCESSING METHOD

CROSS-REFERENCES TO RELATED APPLICATIONS

This application claims priority to Japanese Patent Application No. 2016-120474, filed Jun. 17, 2016, the entirety of which is herein incorporated by reference.

BACKGROUND

1. Technical Field

The present invention relates to a biological information processing device, a program, and a biological information processing method or the like.

2. Related Art

Athletes of sports such as running and cycling have come to carry out heart rate training or the like, for example, as a way of managing exercise loads using biological information such as pulse rate. The aim of introducing exercise load management using biological information is to grasp the load applied to the body, accurately from inside the body using body information, and thus achieve improved efficiency of training and prevention of injuries.

Against this background, there has been progress in measures to acquire the pulse rate. Up to now, measurement using a so-called heart rate sensor worn around the chest with a belt has been a mainstream approach. However, sensors that can acquire the pulse rate when worn around the arm have become commercially available, improving convenience for athletes. Thus, heart rats training has become more widely used as a common training method. However, pulse wave sensors (biological sensors) worn around the arm have the problem of not being able to measure the pulse rate when temperature is low or when the degree of contact between the pulse wave sensor and the arm is low. For example, if the user (subject) cannot check the pulse rate during exercise, the user cannot properly carry out heart rate training or the like.

Particularly the inability to measure the pulse rate when temperature is low cannot be prevented in some cases even if the user takes some measures to handle the situation. For example, there are cases where the pulse rate can be measured immediately after the start of training but about 30 minutes after the training start, the pulse rate can no longer be measured about because the temperature of the pulse wave sensor drops due to the influence of the external temperature.

To cope with this, JP-A-2012-232010 discloses the related-art technique of estimating the pulse rate and presenting the estimated pulse rate to the user when the pulse rate cannot be measured. Specifically, in the related-art technique disclosed in JP-A-2012-232010, the exercise intensity of the subject is computed based on the result of detection by a body motion sensor, and the estimated pulse rate is found based on the resulting exercise intensity. When the pulse rate can be measured with a pulse wave sensor, the measured value is displayed on a display unit. When the pulse rate cannot be measured with the pulse wave sensor, the estimated pulse rate is displayed on the display unit.

The related-art technique disclosed in JP-A-2014-236775 uses an estimated pulse rate as a value to complement the pulse rate when it is determined that the measured pulse rate has low reliability. Specifically, when determining whether the measured pulse rate is appropriate or not, the estimated pulse rate (estimated value of pulse rate) is used as a reference pulse rate for window processing.

In the related-art technique disclosed in JP-A-2015-157128, the pitch of the subject is calculated using the result of detection by a body motion sensor, and an estimated pulse rate is estimated using the pitch.

In the related-art technique disclosed in JP-A-2012-232010, for example, it is assumed that the pulse wave sensor is in operation, as shown in FIG. 7 of this literature. When the pulse wave sensor is not in operation, pulse rate estimation is not carried out and therefore the user cannot grasp the pulse rate.

In the related-art technique disclosed in JP-A-2014-236775, the actually measured pulse rate is used as the initial value of the estimated pulse rate. Therefore, if the measurement of the pulse rate fails even once, the estimated pulse rate cannot be found. In this case, the accuracy of the measured value of pulse rate presented to the user may drop, or it may take time to specify the value.

In the related-art technique disclosed in JP-A-2015-157128, in the case where the measurement of the pulse rate is started during walking or running, if the transition of the pulse rate before the start of the measurement is unknown and the pulse rate and the pitch are similar values, it is difficult to discriminate a body motion component and a pulse rate component included in a mixed manner in a pulse wave signal. Therefore, the pulse rate may not be able to be specified properly. Thus, it may take time to start measuring the pulse rate, or a detection error may occur.

SUMMARY

An advantage of some aspects of the invention is to provide a biological information processing device, a program and a biological information processing method or the like which enable pulse wave information to be found even if pulse wave measurement is not started.

An aspect of the invention relates to a biological information processing device including: a pulse wave sensor which measures a pulse wave of a user; a body motion sensor which detects a body motion of the user; and a processing unit which performs estimation processing for pulse wave information of the user. The processing unit performs the estimation processing based on body motion information acquired using a signal from the body motion sensor, even if the pulse wave sensor is off.

In the aspect of the invention, the estimation processing for estimated pulse wave information of the user is performed based on the body motion information acquired using a signal from the body motion sensor, even if the pulse wave sensor is off. Therefore, the pulse wave information can be found even if pulse wave measurement is not started.

In the aspect of the invention, the processing unit may specify exercise state information indicating an exercise state of the user based on the body motion information, and perform the estimation processing for the pulse wave information based on corresponding relationship information between the exercise state information and the pulse wave information of the user, and the exercise state information.

With this configuration, if the body motion information of the user can be acquired, the pulse wave information can be estimated using the corresponding relationship information.

In the aspect of the invention, the biological information processing device may also include a detection unit which detects at least one user action, of attachment of the biological information processing device to the user, a movement of the user, and an input operation by the user, and the processing unit may start the estimation processing if the user action is detected by the detection unit.

With this configuration, if the user action is not detected, the estimation processing for the pulse wave information is not performed and therefore unnecessary processing can be avoided.

In the aspect of the invention, the processing unit may switch on an operation of the pulse wave sensor after the estimation processing is started.

With this configuration, pulse wave sensor information acquired from the pulse wave sensor can be used for the estimation processing for the pulse wave information.

In the aspect of the invention, the processing unit may find reference pulse wave information of the user by the estimation processing, and perform the estimation processing, based on pulse wave sensor information acquired from the pulse wave sensor whose operation is on, and the reference pulse wave information.

With this configuration, the accuracy of estimation of the pulse wave information can be improved.

In the aspect of the invention, the processing unit may perform intermittent on/off control in which the pulse wave sensor is intermittently switched on/off.

With this configuration, the pulse wave sensor information can be acquired while the electricity consumption by the pulse wave sensor is restrained.

In the aspect of the invention, the processing unit may also perform the estimation processing during an operation-off period in the intermittent on/off control.

With this configuration, the latest pulse wave information can continue to be presented to the user while an increase in electricity consumption is restrained.

In the aspect of the invention, the processing unit may start the estimation processing at a timing before a timing when the operation of the pulse wave sensor is switched on from off.

With this configuration, the pulse wave information can be presented to the user before the pulse wave measurement by the pulse wave sensor is carried out.

In the aspect of the invention, if it is determined that an estimated value of pulse rate found by the estimation processing is in an unchanged state, the processing unit may stop the estimation processing until it is determined that the estimated value of pulse rate is in a changed state.

With this configuration, the number of times the estimation processing is executed can be reduced when there is no need to frequently perform the estimation processing for the pulse wave information.

In the aspect of the invention, the processing unit may perform determination processing in which an exercise state of the user is determined based on the body motion information, stop the estimation processing if it is determined that the exercise state is in an unchanged state from the time of the previous determination processing, and resume the estimation processing if it is determined that the exercise state of the user is in a changed state.

With this configuration, even if the estimation processing for the pulse wave information is stopped, whether to resume the estimation processing for the pulse wave information or not can be determined.

In the aspect of the invention, the processing unit may use the pulse wave information acquired when the estimation processing is stopped, as an initial value, when resuming the estimation processing after the estimation processing is stopped.

With this configuration, re-execution of the estimation processing for the pulse wave information can be avoided.

In the aspect of the invention, the processing unit may perform processing in which at least one item of information from among exercise intensity, target exercise intensity and calories burned, of the user, is specified based on the pulse wave information estimated by the estimation processing, when the operation of the pulse wave sensor is off.

With this configuration, at least one item of information from among the exercise intensity, the target exercise intensity and the calories burned can be presented to the user even if the pulse wave sensor is not switched on.

Another aspect of the invention relates to a program causing a computer to function as each of the foregoing components.

Still another aspect of the invention relates to a biological information processing method including: measuring a pulse wave of a user with a pulse wave sensor; detecting a body motion of the user with a body motion sensor; and performing estimation processing for pulse wave information of the user. The estimation processing is performed based on body motion information acquired using a signal from the body motion sensor, even if the pulse wave sensor is off.

BRIEF DESCRIPTION OF THE DRAWINGS

The invention will be described with reference to the accompanying drawings, wherein like numbers reference like elements.

FIG. 19 is an explanatory view showing the frequency of measuring the pulse rate and the timing of estimation processing for estimated pulse wave information, in each mode.

DESCRIPTION OF EXEMPLARY EMBODIMENTS

Hereinafter, en embodiment will be described. It should be noted that the embodiment described below should not unduly limit the contents of the invention described in the appended claims. Not all the configurations described in the embodiment are essential components of the invention.

1. Example of System Configuration

Figure 1:
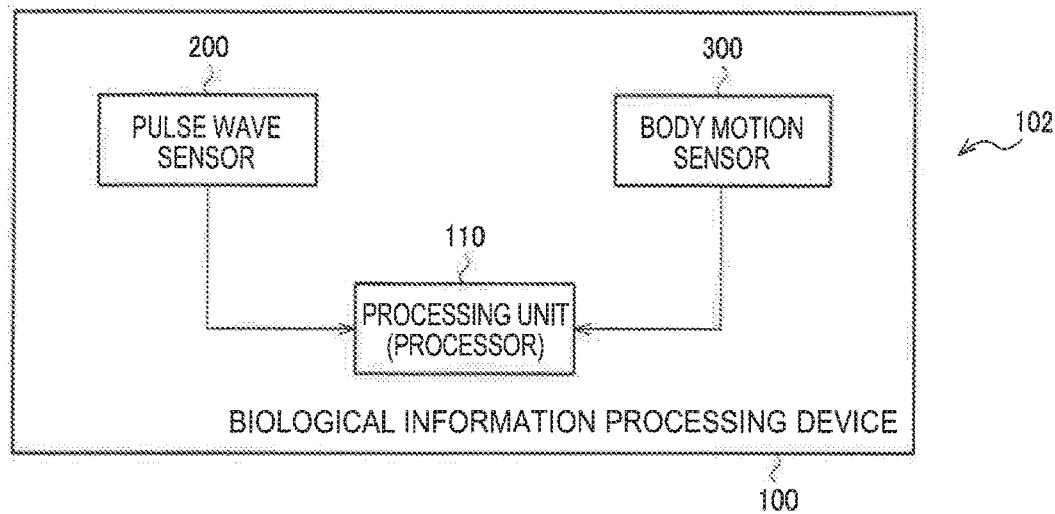
FIG. 1 shows an example of system configuration according to an embodiment.

FIG. 1 shows a biological information processing device 100 according to this embodiment (hereinafter also referred to as a biological information processing system 102), and an example of the configuration of an electronic device including this device. The biological information processing device 100 according to the embodiment includes a processing unit 110 (processor), a pulse wave sensor 200, and a body motion sensor 300. The pulse wave sensor 200 measures a pulse wave of the user. The body motion sensor 300 detects a body motion of the user. The processing unit 110 performs estimation processing for estimated pulse wave information of the user.

The estimated pulse wave information is not pulse wave information which represents pulse rate, pulse wave interval or pulse rate fluctuation acquired by processing a measurement signal from a biological sensor such as a pulse wave sensor or electrocardiograph, but is pulse wave information estimated or calculated based on a history of past pulse wave information and a measurement signal from another type of sensor that cannot directly measure pulse wave information (for example, an acceleration sensor, vibration sensor, pressure sensor or the like).

Figure 2:
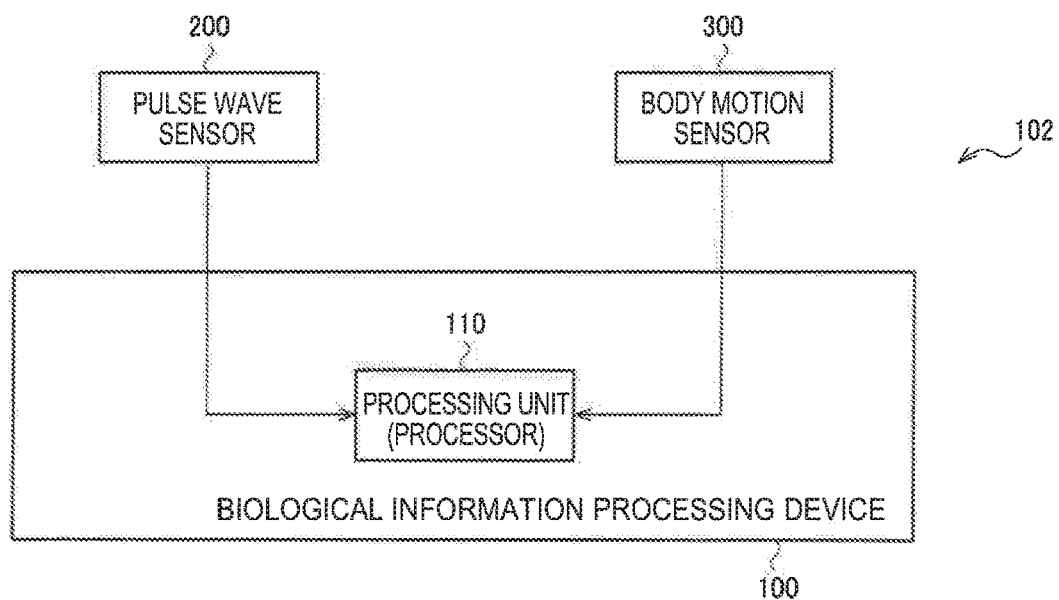
FIG. 2 shows another example of system configuration according to the embodiment.

An example of the biological information processing device 100 or of an electronic device may be a wearable device or the like. The electronic device may include a notification unit or the like (for example, a display unit or audio output unit), not illustrated. A part or the entirety of the functions of the biological information processing device 100 according to the embodiment is realized, for example, by a wearable device. The biological information processing device 100 and the electronic device including this device are not limited to the configuration shown in FIG. 1 and can be implemented with various modifications such as omitting a part of the components or adding another component. For example, as shown in FIG. 2, the biological information processing device 100 includes the processing unit 110, whereas the pulse wave sensor 200 and the body motion sensor 300 can be provided outside the biological information processing device 100.

A part or the entirety of the functions of the biological information processing device 100 (biological information processing system) may be realized by an electronic device (mobile electronic device) that is different from a wearable device such as a smartphone, or by a server system. A specific example of configuration of the biological information processing system will be described later, referring to FIGS. 15 to 17.

For example, as described later with reference to FIG. 15, in the case where the biological information processing device 100 according to the embodiment is realized by a server system 600 and where the server system 600 acquires pulse wave sensor information and body motion information from a wearable device 500 worn by the user, the biological information processing device 100 may include a communication unit which communicates with the wearable device 500 via a network (receiving unit which receives information from the wearable device 500). The communication unit may be a communication device such as a USB connector (communication terminal) or wireless antenna, or may be a processor or the like which controls the communication device.

The pulse wave sensor 200 (pulse wave sensor device) is a sensor for detecting pulse wave information (pulse wave signal) and may be, for example, a photoelectric sensor or the like which is provided in the wearable device 500 attached to the subject and which includes a light emitting unit and a light receiving unit. The pulse wave information is information about the pulse wave of the subject and indicates, for example, the pulse rate (heart rate). The pulse wave sensor information is information acquired from the pulse wave sensor 200. The pulse wave sensor information may be the pulse wave information itself or may be, for example, a waveform signal indicating a pulse wave.

The pulse wave sensor 200 is known to be able to be realized by various sensors such as photoelectric sensor and other types of sensors (for example, ultrasonic sensor). These sensors can be broadly applied to the pulse wave sensor 200 in the embodiment.

The body motion sensor 300 (body motion sensor device) is a sensor which is provided in the wearable device 500 attached to the subject and which can acquire body motion information of the subject. For example, the body motion information is information indicating a body motion of the subject acquired from the body motion sensor 300. The body motion information is information indicating, for example, the moving distance of the subject, number of steps taken, stride, moving time, moving velocity, acceleration, absolute amount of acceleration change, frequency of acceleration change, amount of exercise, content of exercise (content of activity), difference in elevation above sea level per unit time, elevation above sea level, information acquired from a gyro sensor, absolute amount of angular velocity change, frequency of angular velocity change, information acquired from a geomagnetic sensor, absolute amount of geomagnetism change, frequency of geomagnetism change, and information acquired form a barometric pressure sensor signal. In the embodiment, it is recommended that these pieces of information should be handled as multi-dimensional vectors. However, similar information may be omitted in order to reduce the volume of information.

As the body motion sensor 300, for example, an acceleration sensor or the like can be used. In this case, the processing unit 110 acquires acceleration information (or location information) as body motion information from the acceleration sensor. The body motion sensor 300 may also be a gyro sensor, altitude sensor, geomagnetic sensor, barometric pressure sensor, or the like. Moreover, the body motion sensor 300 may be, for example, a GPS (Global Positioning System) receiver or the like. In this case, the GPS receiver (body motion sensor 300) acquires location information indicating the current location of the wearable device 500 (subject), based on radio waves transmitted from GPS satellites. The processing unit 110 acquires the location information of the wearable device 500 (subject) as body motion information.

The processing unit 110 performs the estimation processing for the estimated pulse wave information of the subject, based on the body motion information acquired from the body motion sensor 300, even in the case where the pulse wave sensor 200 is off. The functions of the processing unit. 110 can be realized by hardware such as various processors (CPU or the like) and ASIC (gate array or the like), or by a program or the like. For example, in the example shown in FIG. 1, the processor realizes the functions of the processing unit 110. However, this embodiment is not limited to this example and various modifications can be made. For example, the biological information processing device 100 (biological information processing system 102) may include a plurality of processors, and the plurality of processors may realize the functions of the processing unit 110.

Here, the case where the pulse wave sensor 200 is off includes not only the state where no electricity is supplied to the pulse wave sensor 200 but also the state where the electricity consumption by the pulse wave sensor 200 is smaller than at the time of measurement. Alternatively, the case where the pulse wave sensor 200 is off may be the state where no signal is outputted from the pulse wave sensor 200, or the state where the processing unit 110 is not carrying out the calculation of pulse wave information using a signal from the pulse wave sensor 200.

In the case where the pulse wave sensor 200 is off, the processing unit 110 in the embodiment can find the pulse rate of the subject as a measured value (hereinafter referred to as measured pulse rate), based on the pulse wave information acquired from the pulse wave sensor. In this case, the processing unit 110 can find the estimated pulse rate by performing the estimation processing for estimated pulse wave information based on the body motion information acquired from the body motion sensor 300. The processing unit 110 can then use the estimated pulse rate, thus found, for correction processing for the measured pulse rate, or can display the estimated pulse rate with the measured pulse rate on a display unit, not illustrated. Moreover, in the embodiment, even in the case where the pulse wave sensor 200 is off, the processing unit 110 performs the estimation processing for estimated pulse wave information, based on the body motion information acquired from the body motion sensor 300, as described above. Thus, even in the case where pulse wave measurement is not started, the estimated pulse rate can be found.

It is not always the case that the estimated pulse rate cannot be found unless the pulse rate is measured, as in JP-A-2014-236775. Therefore, even in the case where the pulse wave sensor is not in operation, the estimated pulse rate can be presented to the user. Also, in the case where the pulse wave sensor is put into operation, the estimated pulse rate can be presented to the user before the pulse rate is measured by the pulse wave sensor, and therefore the waiting time of the user can be reduced. Moreover, if the pulse rate is measured, using the estimated pulse rate estimated before the start of pulse rate measurement as a reference value, the measurement can be completed more quickly than in the case of measuring the pulse rate without using any reference value. Therefore, the electricity consumption required for the measurement of the pulse rate can be reduced.

Moreover, it is not always the case that the pulse rate cannot be properly specified during walking or running if pulse rate measurement is started during walking or running, as in JP-A-2015-157128. Even during walking or running, the estimated pulse rate can be estimated and presented to the user, just as when the user is in other activity states.

In the embodiment, the following configuration may be employed as well. That is, the biological information processing device 100 includes a memory (storage unit) which stores information (for example, programs and various data), and a processor (processing unit 110, processor configured with hardware) which operates based on the information stored in the memory. The processor acquires body motion information of the subject from the body motion sensor 300 (body motion sensor device) provided in the wearable device 500. The processor then performs the estimation processing for the estimated pulse wave information of the user, based on the body motion information.

The functions of the individual parts of the processor (processing unit 110) may be realized by individual pieces of hardware, for example. Alternatively, the functions of the individual parts may be realized by integrated hardware. The processor may be a CPU (central processing unit), for example. However, the processor is not limited to a CPU and can be various other processors such as GPU (graphics processing unit) or DSP (digital signal processor). The processor may also be a hardware circuit based on an ASIC (application specific integrated circuit). The memory (storage unit) may be, for example, a semiconductor memory such as SRAM (static random access memory) or DRAM (dynamic random access memory), a register, a magnetic storage device such as a hard disk device, or an optical storage device such as an optical disc device. For example, the memory stores computer-readable commands, and the functions of the processing unit 110 are realized by having the commands executed by the processor. The commands in this case may be commands in a command set that forms a program, or may be commands that instruct the hardware circuit of the processor to perform operations.

2. Technique in Embodiment

Next, the technique in the embodiment will be described. In the embodiment, the processing unit 110 performs the estimation processing for the estimated pulse wave information of the subject based on the body motion information acquired from the body motion sensor 300, even in the case where the pulse wave sensor 200 is off, as described above. In this case, the processing unit 110 specifies exercise state information indicating the exercise state of the user, based on the body motion information, and performs the estimation processing for estimated pulse wave information, based on corresponding relationship information between the exercise state information and the estimated pulse wave information of the user, and the exercise state information.

Here, the exercise state refers to the state, degree and the like of exercise (activity) carried out by the user, for example, a running state or walking state (moving state), ascending/descending state, moving velocity, oxygen intake (oxygen consumption), exercise intensity, described later, or the like. The information indicating this exercise state is referred to as exercise state information. For example, FIG. 3, described later, shows the case where the exercise state is the moving velocity.

Figures 3, 4:
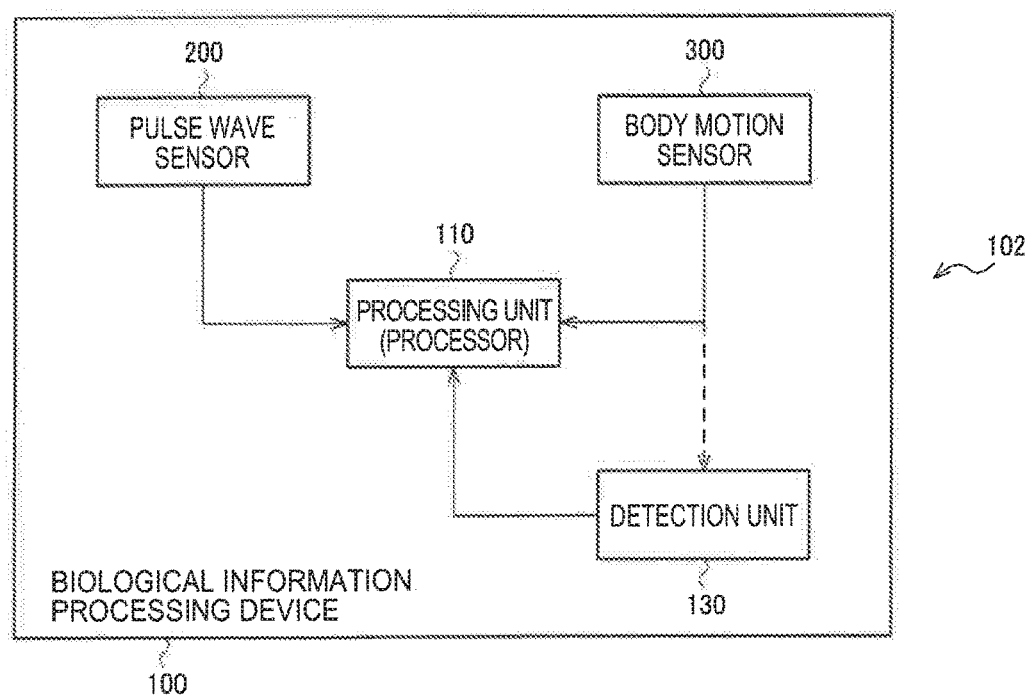
FIG. 3 is an explanatory view showing corresponding relationship information between exercise state information and estimated pulse wave information.
FIG. 4 shows another example of system configuration according to the embodiment.

The corresponding relationship information between the exercise state information and the estimated pulse wave information refers to information indicating the corresponding relationship between a certain exercise state and the estimated pulse rate of the user estimated at that time. FIG. 3 shows a specific example of the corresponding relationship information. In the example shown in FIG. 3, $hr_0$ to $hr_1$ as the pulse rate (estimated pulse rate) of the user corresponds to the velocity (moving velocity) $v_0$ to $v_1$ of the user. Similarly, $hr_1$ to $hr_2$ as the estimated pulse rate corresponds to the velocity $v_1$ to $v_2$, and $hr_2$ to $hr_3$ as the estimated pulse rate corresponds to the velocity $v_2$ to $v_3$, and $hr_3$ to $hr_4$ as the estimated pulse rate corresponds to the velocity $v_3$ to $v_4$. In this way, in the example shown in FIG. 3, the table information which establishes the correspondence between the moving velocity and the estimated pulse rate of the user is the corresponding relationship information.

Thus, if the body motion information of the user can be acquired, the estimated pulse wave information can be estimated using the corresponding relationship information as shown in FIG. 3. The corresponding relationship information like this can be updated as a learning table (learning result), for example, by learning based on the exercise state of the user and the measured pulse wave information (measured pulse rate) or the like. If the leaning is repeated, more accurate corresponding relationship information can be obtained and the accuracy of estimation of the estimated pulse wave information can be improved.

The learning table shown in FIG. 3 illustrates the association between the estimated pulse wave information and the velocity of the user. However, the embodiment is not limited to this example. For example, in the learning, the result of analysis of an acceleration signal such as the frequency, amplitude and pitch (number of steps taken per minute) of an acceleration signal acquired from an acceleration sensor, may be associated with the estimated pulse wave information. With this configuration, there is no need to analyze the body motion signal from the body motion sensor 300 and derive body motion information such as velocity, and the estimated pulse wave information can be acquired based on signal characteristics of the body motion signal. Therefore, the estimated pulse wave information can be acquired by simpler processing.

Moreover, the learning table may be a table in which the moving velocity acquired using the GPS is associated with the estimated pulse wave information, or may be a table in which an indicator indicating the exercise state (moving velocity, gradient or the like) generated based on information acquired from both the GPS and the acceleration sensor is associated with the estimated pulse wave information.

Next, the timing of starting the estimation processing for estimated pulse wave information will be described. For example, in the case where the user does not wear the biological information processing device 100, the estimation processing for estimated pulse wave information cannot be performed. Also, if the user is in the same attitude for a long period of time, it is often the case that the pulse wave information is not changed very much and that there is little need to perform the estimation processing for estimated pulse wave information.

Thus, the biological information processing device 100 in the embodiment may include a detection unit 130, as shown in FIG. 4. The detection unit 130 detects at least one user action, of the attachment of the biological information processing device 100 to the user, a movement of the user, and an input operation by the user. The processing unit 110 starts the estimation processing for estimated pulse wave information if the user action is detected by the detection unit 130.

Figure 5:
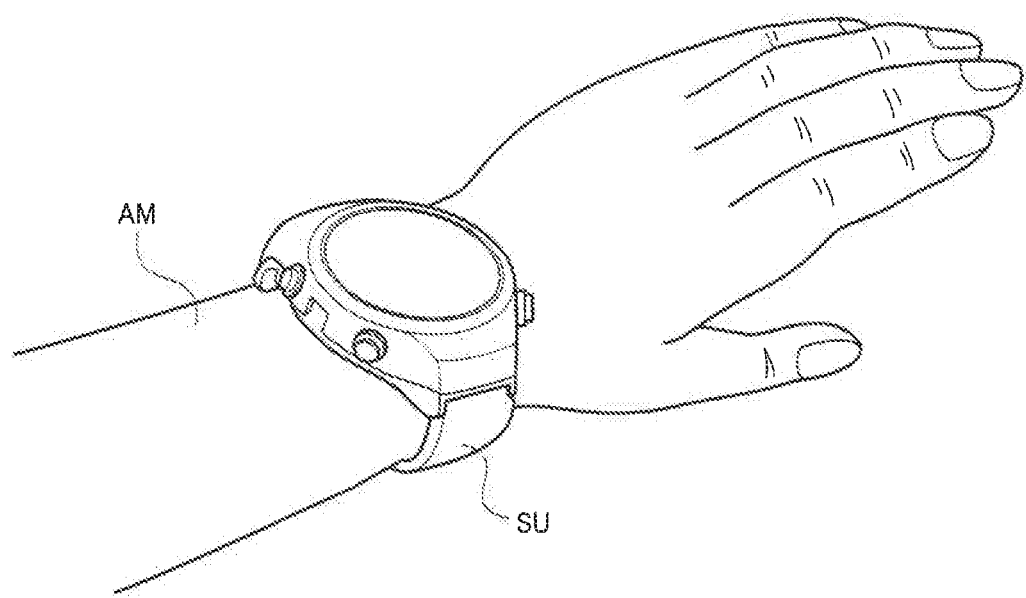
FIG. 5 is an explanatory view of a user action.
Figure 6:
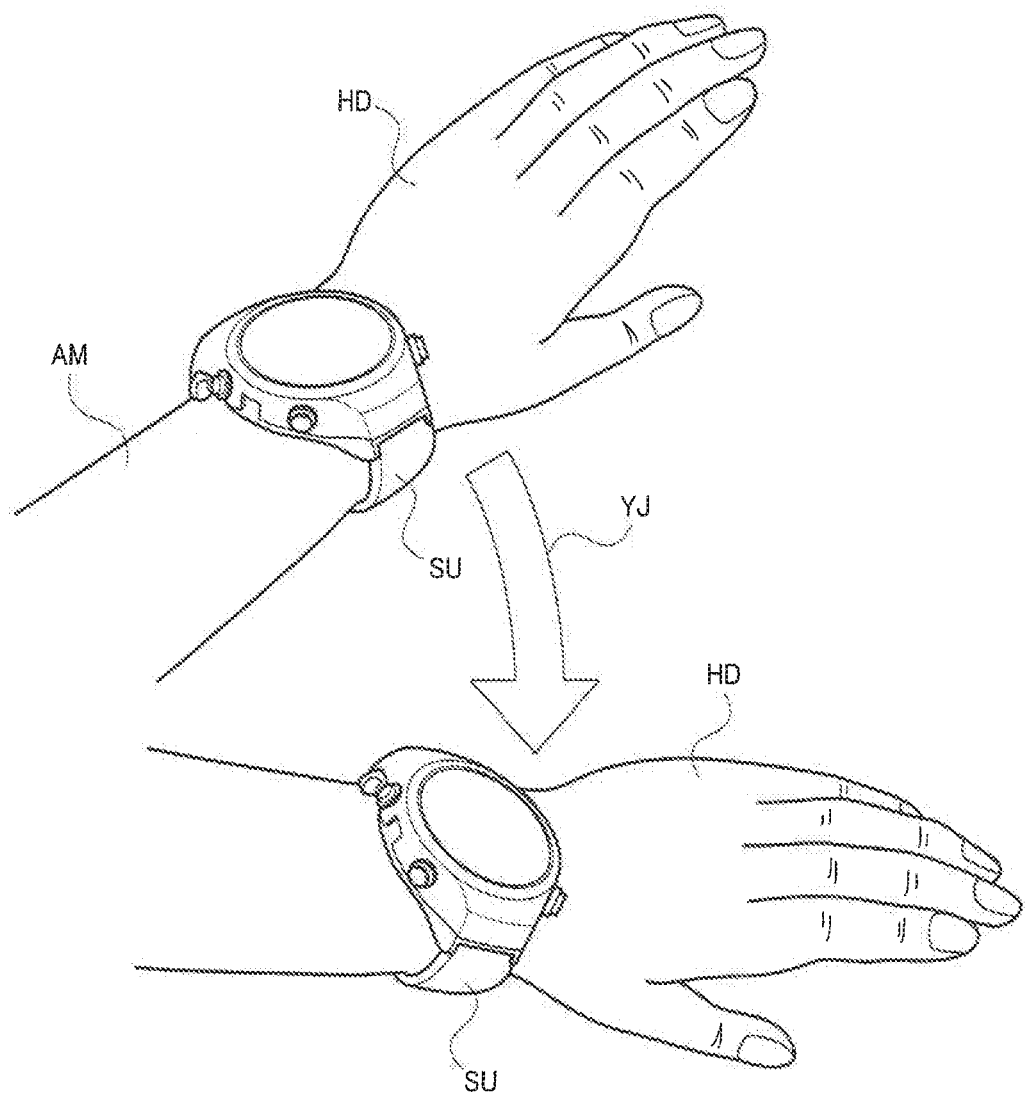
FIG. 6 is another explanatory view of a user action.
Figure 7:
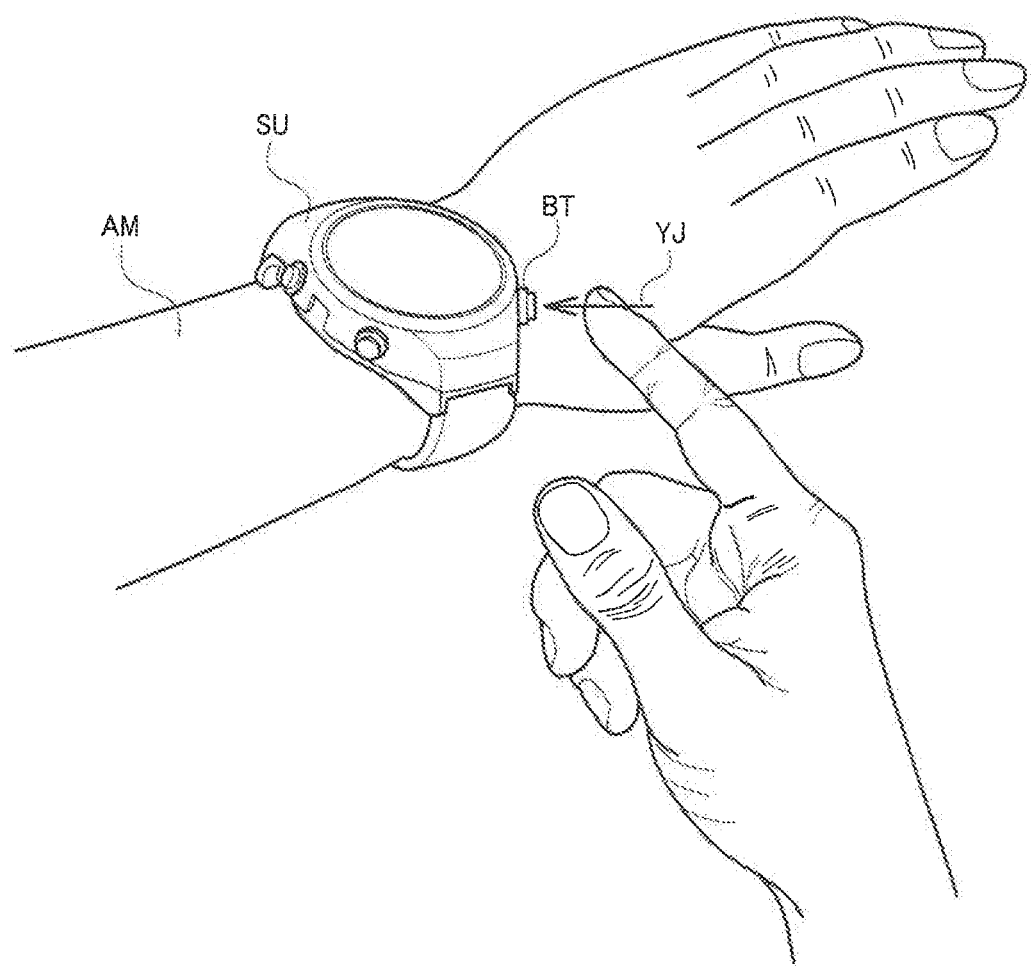
FIG. 7 is another explanatory view of a user action.

Specific examples of the user action are shown in FIGS. 5 to 7. In the example shown in FIG. 5, the user wears a wristwatch-type biological information processing device SU on an arm AM. For example, in the case as shown in FIG. 5, the detection unit 130 has an optical sensor or the like provided, for example, on the back side (side facing the subject when the device is worn) of the case unit of the wristwatch-type biological information processing device SU. The detection unit 130 thus determines whether the wristwatch-type biological information processing device SU is worn or not, based on sensor information acquired from the optical sensor, and notifies the processing unit 110 of the result of the determination.

In the example shown in FIG. 6, the user wearing the wristwatch-type biological information processing device SU on the arm AM is moving a hand HD as indicated by an arrow YJ. In the case as shown in FIG. 6, the detection unit 130 acquires body motion information from the body motion sensor 300 as indicated by a dotted line in FIG. 4, then determines whether the user has carried out a predetermined action or not based on the acquired body motion information, and notifies the processing unit 110 of the result of the determination.

In the example shown in FIG. 7, the user is operating the wristwatch-type biological information processing device SU, by pressing a button BT (operation unit, switch) provided on the wristwatch-type biological information processing device SU with a finger as indicated by an arrow YJ, for example, in order to give an instruction (request) to perform the estimation processing for estimated pulse wave information. In this case, the detection unit 130 detects whether the button BT in FIG. 7 is operated or not, and notifies the processing unit 110 of information indicating the operation content if the operation on the button BT is detected. Alternatively, the detection unit 130 may detect a tap on the case of the wristwatch-type biological information processing device SU with a finger. The processing and functions of the detection unit 130 may also be implemented by the processing unit 110.

In the embodiment, the estimation processing for estimated pulse wave information is performed if one of such user actions is detected. That is, the estimation processing for estimated pulse wave information can be performed immediately after the user puts on the biological information processing device, or when the user has moved the body, or when a request to perform the estimation processing for estimated pulse wave information is made by the user. In other words, if none of the user actions is detected, the estimation processing for estimated pulse wave information is not performed and therefore unnecessary processing can be avoided.

Next, the case where pulse wave measurement is carried out using the pulse wave sensor 200 will be described. The accuracy of the estimated pulse wave information can be improved further if the estimated pulse wave information is corrected using pulse wave information that is actually measured. Thus, the processing unit 110 switches on the operation of the pulse wave sensor 200 after the estimation processing is started.

Thus, the pulse wave sensor information acquired from the pulse wave sensor 200 can be used for the estimation processing for estimated pulse wave information.

For example, the processing unit 110 finds reference pulse wave information of the user by estimation processing, and performs estimation processing based on the pulse wave sensor information acquired from the pulse wave sensor 200 whose operation is switched on and the reference pulse wave information.

The reference pulse wave information is pulse wave information used as a reference when finding the estimated pulse wave information. The reference pulse wave information is, for example, pulse wave information when the user is at rest, and can be found using the corresponding relationship information described with reference to FIG. 3.

Thus, the accuracy of estimation of the estimated pulse wave information can be improved.

If the pulse wave sensor information acquired from the pulse wave sensor 200 is used in this way, the accuracy of estimation of the estimated pulse wave information can be improved. However, if the pulse wave sensor 200 is constantly on, electricity consumption increases. Also, the pulse wave sensor information need not necessarily be acquired constantly but needs to be acquired to correct the estimated pulse wave information, for example, every predetermined period.

Thus, the processing unit 110 performs intermittent on/off control in which the pulse wave sensor 200 is intermittently switched on/off. In the intermittent on/off control, for example, a series of operations of switching on the pulse wave sensor 200 for a first period (operation-on period), then switching off the pulse wave sensor 200 for a second period (operation-off period) and subsequently switching on the pulse wave sensor 200 again is repeated. The first period and the second period may be fixed periods or may be periods that can be variably set.

Thus, the pulse wave sensor information can be acquired while the electricity consumption by the pulse wave sensor 200 is restrained.

Meanwhile, the processing unit 110 also performs the estimation processing for estimated pulse wave information during the operation-off operation in the intermittent on/off control. In the embodiment, the estimated pulse wave information is found, for example, using the body motion information and the corresponding relationship information, as described above, and therefore can be found without the pulse wave sensor information. Often, it suffices for the user to be able to check at least the estimated pulse wave information, without being able to check the actually measured pulse wave information. Moreover, compared with the case where the pulse wave sensor 200 is constantly driven, the increase in electricity consumption does not pose a serious problem even if the processing unit 110 is driven to perform the estimation processing for estimated pulse wave information.

Thus, the latest estimated pulse wave information can continue to be presented to the user while the increase in electricity consumption is restrained. In that case, the processing unit 110 displays the estimated pulse wave information, for example, on a display unit, not illustrated.

As described above, in JP-A-2012-232010, pulse wave estimation is not carried out if the pulse wave sensor is not in operation. Therefore, in order to know the pulse rate, the user has to wait until the pulse wave measurement by the pulse wave sensor is finished. The user cannot know the pulse rate immediately after wearing the biological information processing device.

In contrast, in the embodiment, the processing unit 110 starts the estimation processing for estimated pulse wave information if a user action is detected by the detection unit 130, as described above. In other words, the processing unit 110 starts the estimation processing at a timing before the timing when the operation of the pulse wave sensor 200 is switched on from off.

Thus, the estimated pulse wave information can be presented to the user before the pulse wave measurement by the pulse wave sensor is carried out.

Next, the timings of stopping and resuming the estimation processing for estimated pulse wave information will be described. Often, the estimated pulse rate (estimated value of pulse wave) does not change very much when the user is at rest. It can be said that, in such a case, there is little need to perform the estimation processing for estimated pulse wave information at the same frequency as in the case where the estimated pulse changes greatly.

Thus, if it is determined that the estimated value of pulse rate found by the estimation processing is in an unchanged state, the processing unit 110 stops the estimation processing until it is determined that the estimated value of pulse rate is in a changed state.

The unchanged state in this case refers to the state where the difference between the estimated value of pulse rate found by the previous estimation processing and the estimated value of pulse rate found by the current estimation processing is within a predetermined range. The changed state refers to that the difference between the estimated value of pulse rate found by the previous estimation processing and the current estimated value of pulse rate is equal to or above a predetermined threshold.

Thus, the number of times the estimation processing is executed can be reduced in the case where the estimation processing for estimated pulse wave information need not be performed frequently.

However, in the case where the estimation processing for estimated pulse wave information is stopped, whether the estimated value of pulse rate is in the changed state or not cannot be determined by direct comparison of the estimated value of pulse rates, when determining the timing of resuming the estimation processing.

Thus, the processing unit 110 performs determination processing in which the exercise state of the user is determined, based on the body motion information. If the processing unit 110 determines that the exercise state is in the unchanged state from the time of the previous determination processing, the processing unit 110 stops the estimation processing. Then, if the processing unit 110 determines that the exercise state of the user has become the changed state, based on the body motion information, the processing unit 110 resumes the estimation processing. That is, if the processing unit 110 determines that the exercise state is in the unchanged state from the time of the previous determination processing, the processing unit 110 regards the estimated value of pulse rate as being in the unchanged state and stops the estimation processing. If the processing unit 110 determines that the exercise state of the user has become the changed state, the processing unit 110 regards the estimated value of pulse rate as being in the changed state and resumes the estimation processing. Here, the exercises state being in the unchanged state refers to, for example, the state where the user is in a walking state with his/her walking pace or the like unchanged. The exercise state being in the changed state refers to, for example, the state where the user has shifted from a walking state to a running state.

Thus, even in the case where the estimation processing for estimated pulse wave information is stopped, whether the estimated value of pulse rate has turned into the changed state or not can be determined and whether to resume the estimation processing for estimated pulse wave information or not can be determined. Modifications such as regarding the estimated value of pulse rate as being in the changed state and resuming the estimation processing for estimated pulse wave information if a user action is detected, as described above, can be carried out as well.

The processing unit 110 then uses the estimated pulse wave information at the time when the estimation processing is stopped, as an initial value when resuming the estimation processing after the estimation processing is stopped. That is, the estimation processing is resumed, based on the previously estimated pulse wave information.

Using the most recent estimated pulse wave information when resuming the estimation processing for estimated pulse wave information, re-execution of the estimation processing from the point when the user is at rest can be avoided.

Also, in the case where the operation of the pulse wave sensor 200 is off, the processing unit 110 performs processing in which at least one piece of information from among the exercise intensity, target exercise intensity and calories burned, of the user, is specified based on the estimated pulse wave information estimated by the estimation processing.

Here, the exercise intensity (activity intensity) is, for example, a numerical value or the like indicating the intensity of the exercise (activity) carried out by the subject. Specifically, METs (metabolic equivalents), the pace (min/km) of running (moving) or the like may be employed. The target exercise intensity is the exercise intensity to be achieved when the user carries out exercise. The target exercise intensity is decided based on the current exercise intensity, calories burned, duration of exercise, physical strength of the user, target information inputted by the user, or the like.

Thus, at least one piece of information, of the exercise intensity, target exercise intensity, and calories burned, can be presented to the user without having to switch on the pulse wave sensor 200. In that case, the processing unit 110 displays the information, for example, on a display unit, not illustrated.

The embodiment can also be applied to a biological information processing method including: measuring a pulse rate of a user with the pulse wave sensor 200; detecting a body motion of the user with the body motion sensor 300; and performing estimation processing for estimated pulse wave information of the user, wherein the estimation processing is performed based on body motion information acquired from the body motion sensor 300, even if the pulse wave sensor 200 is off.

3. Details of Processing

Next, details of the processing in the embodiment will be described with reference to the flowchart of FIG. 8.

First, the processing unit 110 acquires body motion information from the body motion sensor 300 (S101). Next, the processing unit 110 determines whether the user action is detected by the detection unit 130 or not, based on the acquired body motion information (S102). If the processing unit 110 determines that the user action is not detected by the detection unit 130 (NO in S102), the processing unit 110 repeats the processing of Steps S101 to S102 until the user action is detected. In this case, the processing of Steps S101 to S102 is carried out, for example, every predetermined period.

Meanwhile, if the processing unit 110 determines that the user action is detected by the detection unit 130 (YES in S102), the processing unit 110 determines whether to stop or resume the estimation processing for estimated pulse wave information or not (S103). If the processing unit 110 determines that the estimation processing is to be stopped (YES in S103), the processing unit 110 ends the series of processing. The flow of the processing of Step S103 will be described later with reference to the flowcharts of FIGS. 9 and 10.

If the processing unit 110 determines that the estimation processing is not to be stopped (NO in S103), the processing unit 110 acquires corresponding relationship information between exercise state information and estimated pulse wave information from a storage unit or the like, not illustrated (S104). The processing unit 110 then specifies the exercise state information indicating the exercise state of the user, based on the body motion information, and performs the estimation processing for estimated pulse wave information, based on the corresponding relationship information and the exercise state information (S105).

Next, the processing unit 110 performs control to intermittently switch on/off the operation of the pulse wave sensor 200 (S106). The processing unit 110 then determines whether the operation of the pulse, wave sensor 200 is set in on-state or not (S107). If the processing unit 110 determines that the operation of the pulse wave sensor 200 is set in on-state (YES in S107), the processing unit 110 acquires pulse wave sensor information from the pulse wave sensor 200 (S108). Next, the processing unit 110 finds reference pulse wave information based on the acquired pulse wave sensor information (S109) and performs the estimation processing for estimated pulse wave information, based on the pulse wave sensor information and the reference pulse wave information (S110). The processing unit 110 then returns to the processing of Step S101.

Meanwhile, if the processing unit 110 determines that the operation of the pulse wave sensor 200 is set in off-state (NO in S107), the processing unit 110 returns to Step S101 without performing the processing of Steps S108 to S110.

Next, a detailed flow of the processing of Step S103 in FIG. 8 will be described with reference to the flowchart of FIG. 9.

First, the processing unit 110 compares the previously estimated value of pulse rate stored in a storage unit, not illustrated, with the currently estimated value of pulse rate (S201). Next, processing unit 110 determines whether the estimated value of pulse rate is in an unchanged state or not (S202). If the processing unit 110 determines that the estimated value of pulse rate is in the unchanged state (YES in S202), the processing unit 110 determines that the estimation processing is to be stopped (S203). Meanwhile, if the processing unit 110 determines that the estimated value of pulse rate is not in the unchanged state (NO in S202), the processing unit 110 determines that the estimation processing is not to be stopped (S204). In the first and second rounds of execution, the two values of the previously estimated value of pulse rate and the currently estimated value of pulse rate cannot be acquired. Therefore, for example, the previously estimated value of pulse rate and the currently estimated value of pulse rate are regarded as different values and it is determined that the estimation processing is not to be stopped.

Figure 8:
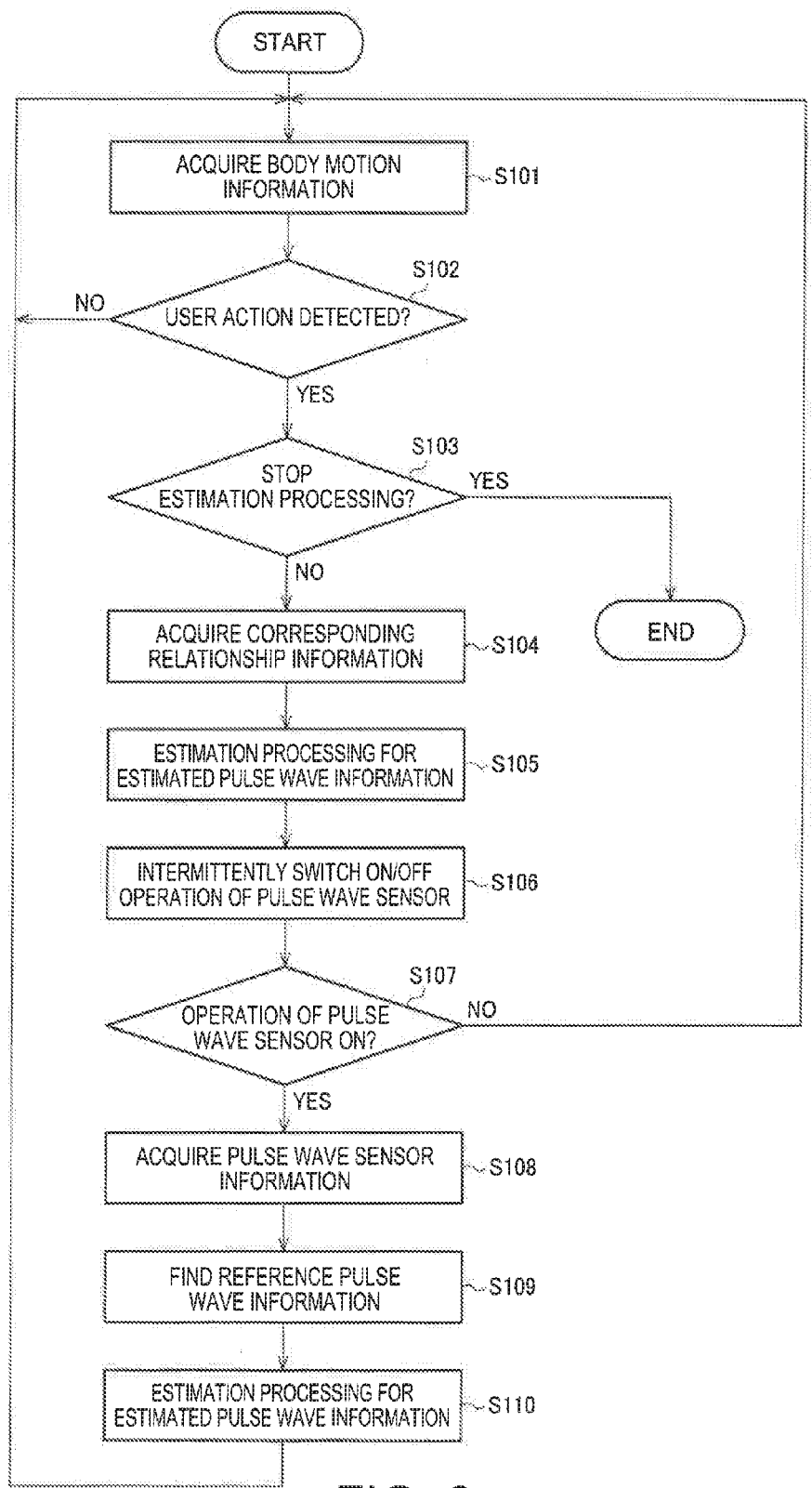
FIG. 8 is a flowchart for explaining a flow of processing according to the embodiment.
Figure 9:
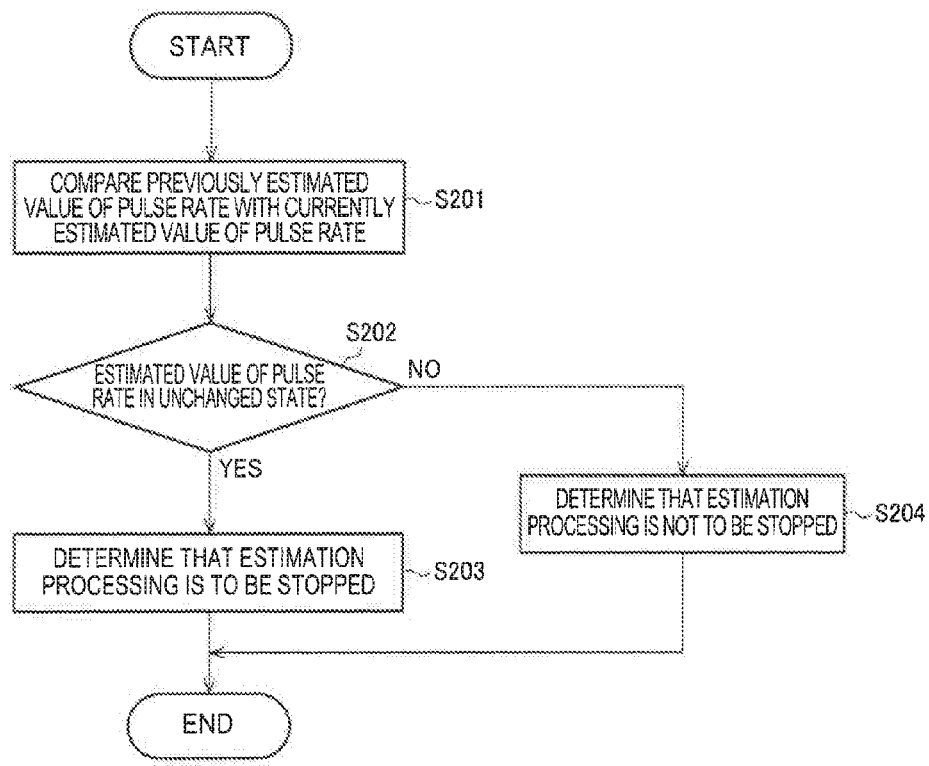
FIG. 9 is a flowchart for explaining a flow of determination processing to determine whether to stop or resume estimation processing.
Figure 10:
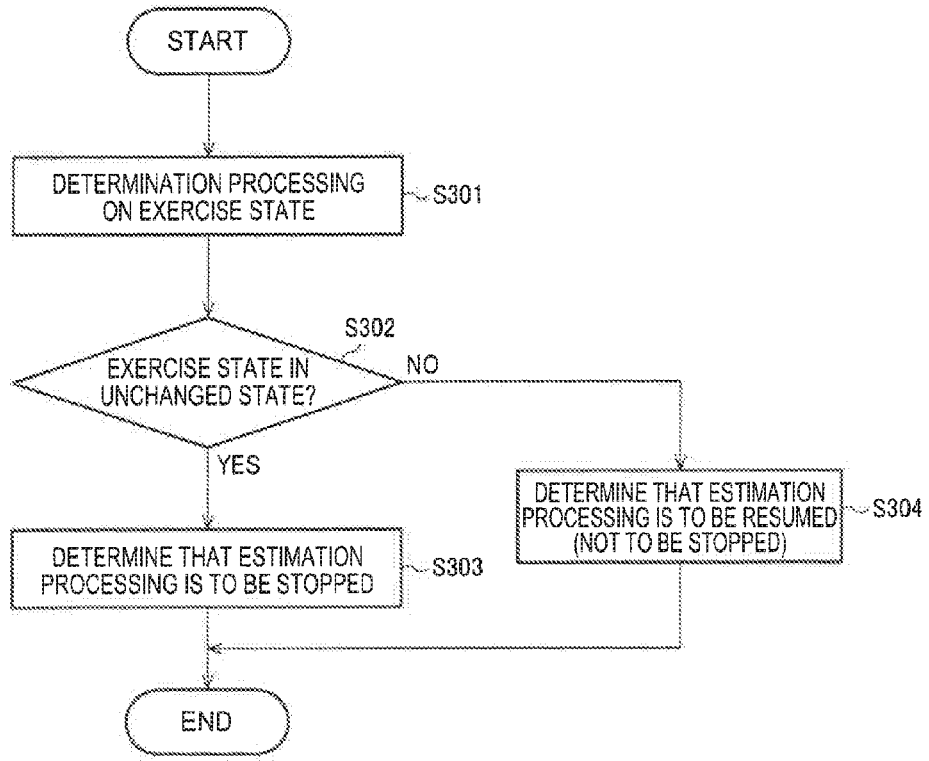
FIG. 10 is another flowchart for explaining a flow of determination processing to determine whether to stop or resume estimation processing.

The processing of Step S103 in FIG. 8 can also be realized by the processing shown in the flowchart of FIG. 10.

In the example shown in FIG. 10, first, the processing unit 110 performs determination processing on the exercise state, based on the body motion information of the user (S301). Next, the processing unit 110 determines whether the exercise state is in an unchanged state or not (S302). If the processing unit 110 determines that the exercise state is in the unchanged state (YES in S302), the processing unit 110 determines that the estimation processing is to be stopped (S303). Meanwhile, if the processing unit 110 determines that the exercise state is not in the unchanged state (NO in S302), the processing unit 110 determines that the estimation processing is to be resumed (not to be stopped) (S304). In the first and second rounds of execution, whether the exercise state is in the unchanged state or not cannot be determined and therefore it is determined that the estimation processing is not to be stopped.

Also, even if the exercise state is in the unchanged state, the estimated value of pulse rate should be calculated in some cases. Such cases include, for example, where the pulse rate needs to be measured in order to analyze the sleep state or the stress level in everyday life.

Figure 18:
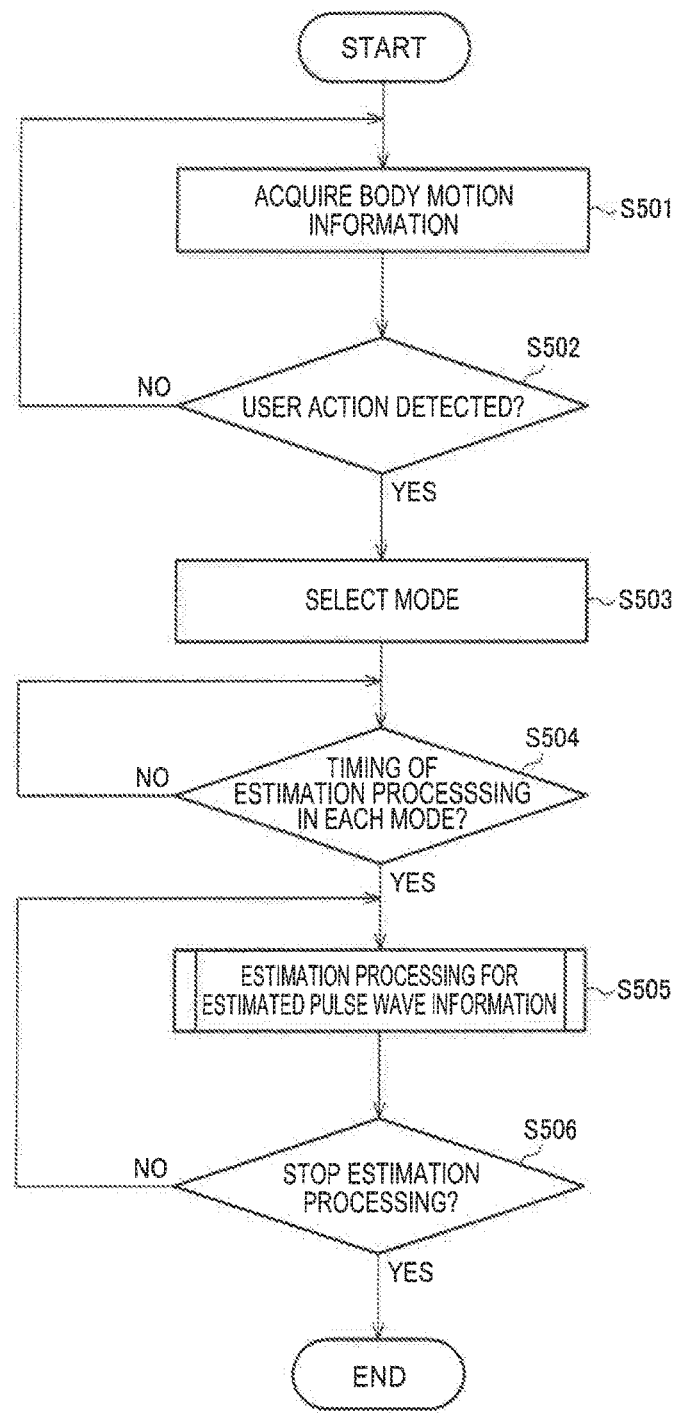
FIG. 18 is a flowchart for explaining a flow of processing when selecting a mode based on a user action.

The flow of processing in such cases is shown in the flowchart of FIG. 18. First, the processing unit 110 acquires body motion information from the body motion sensor 300 (S501). Next, the processing unit 110 determines whether the user action is detected or not, based on the body motion information (S502). If the processing unit 110 determines that the user action is not detected (NO in S502), the processing unit 110 returns to Step S501.

Meanwhile, if the processing unit 110 determines that the user action is detected (YES in S502), the processing unit 110 selects a mode for the estimation processing for estimated pulse wave information (S503). For example, the mode selected in this step is one of the five types of modes shown in the graph of FIG. 19, specifically, one of exercise mode, everyday-life mode, rest mode, sleep mode, and mental measurement mode.

After selecting a mode, the processing unit 110 then determines whether it is the timing of the estimation processing for estimated pulse wave information in the selected mode or not (S504). Specifically, as shown in the table of FIG. 19, for example, if the exercise mode is selected, the start of the exercise is the timing of the estimation processing, and if the other modes are selected, five seconds before the start of the measurement of pulse wave information by the pulse wave sensor 200 is the timing of the estimation processing. If the processing unit 110 determines that it is not the timing of the estimation processing, the processing unit 110 repeats the determination until the timing of the estimation processing comes (NO in S504).

If the processing unit 110 determines that it is the timing of the estimation processing (YES in S504), the processing unit 110 performs the estimation processing for estimated pulse wave information (S505). The processing of Step S505 is equivalent to the processing of Steps S104 to S110 in FIG. 8. The processing of Step S505 includes the pulse wave measurement by the pulse wave sensor 200. At this time, the timing of the pulse wave measurement by the pulse wave sensor 200 varies depending on the selected mode. For example, as shown in the table of FIG. 19, if the exercise mode is selected, the pulse wave measurement is carried out once every second. In the everyday-life mode and the mental measurement mode, the pulse wave measurement is carried out once every minute. In the sleep mode, in which the change in pulse waves is considered to be little, the pulse wave measurement is carried out once every five minutes. In the rest mode, the pulse wave measurement is carried out once every ten minutes.

The processing unit 110 then determines whether to stop the estimation processing for estimated pulse wave information or not (S506). If the processing unit 110 determines that the estimation processing is not to be stopped (NO in S506), the processing unit 110 returns to Step S505. If the processing unit 110 determines that the estimation processing is to be stopped (YES in S506), the processing unit 110 ends the processing.

In this way, if the processing described with reference to FIG. 18 is carried out and estimated pulse wave information is estimated in advance, the time taken for the pulse wave measurement can be reduced and a reduction in electricity consumption can be realized.

4. Modifications

For example, in the case where a photoelectric sensor is used as the pulse wave sensor 200, at the time of analyzing a photoelectric pulse wave signal (pulse wave sensor information, hereinafter also referred simply as a pulse signal) acquired from the photoelectric sensor, the irregularity of the pulse wave due to the influence of body motions may disturb accurate analysis. Particularly, a wrist-wearing device which takes user-friendliness for the subject (user) into consideration is susceptible to the influence of various body motions.

For the analysis of the photoelectric pulse wave, for example, a technique such as finding the pulse wave period and analyzing its fluctuation is used. Therefore, it is basically desirable that a correct pulse wave signal is acquired at any time.

However, in performing pulse analysis in everyday life, it is a matter of course that body motions are present to a certain extent, and the irregularity of the pulse wave due to such body motions is unavoidable.

Therefore, in performing pulse analysis, proper measures need to be taken, such as eliminating phases where such body motions are detected, from the pulse signal analysis target, or lowering the degree of importance of the result of analysis on such phases. To this end, it is necessary to accurately grasp phases where body motions that can pose a problem are detected.

There are various body motions. For example, in the case where the subject carries out periodic exercise such as walking or running, a periodic leakage signal that is hard to distinguish from the pulse is generated. Also, in phases of housework or the like, a short-time impulsive leakage occurs irregularly.

Traditionally, a pulse wave device like this includes a built-in acceleration sensor and thus grasps body motions. In many cases, the acceleration sensor is used to recognize periodic exercise such as walking or running and eliminate a leakage in the pulse in that period. With respect to a short-time impulsive leakage, the acceleration sensor is used to grasp the magnitude of the amount of body motions and determine that the reliability of the pulse is low if the magnitude exceeds a prescribed value.

However, particularly with respect to non-periodic body motions, a body motion with a large amount of acceleration does not necessarily tend to cause the irregularity of the pulse signal. Also, even with a body motion of the same intensity, the degree of influence may vary depending on the intensity of the pulse signal at the time. For these reasons, a preferable grasping method is not known. Therefore, even if the actual leakage into the pulse is small, a pulse signal with no problem in its quality may be invalidated because the amount of acceleration exceeds a predetermined value. Conversely, even if the amount of acceleration is below a predetermined amount, a harmful leakage occurs in the pulse signal because the optical influence is large. Consequently, problems such as performing incorrect analysis may arise.

Thus, in this modification, it is made possible to more properly grasp phases where there is a harmful body motion actually causing the irregularity of the pulse signal. This enables accurate pulse analysis.

Specifically, in this modification, in order to enable grasping phases where there is a harmful body motion actually causing the irregularity of the pulse signal, reliability determination processing on the pulse signal is carried out before performing the estimation processing for estimated pulse wave information. More specifically, the spectral entropy of an acceleration signal acquired from an acceleration sensor (body motion sensor 300) and the spectral entropy of a pulse signal acquired from the pulse wave sensor 200 are found, and the spectral entropy of the acceleration signal is compared with the spectral entropy of the pulse signal over every predetermined time range. Thus, the reliability of pulse signals is determined and a pulse signal with low reliability is not used for the estimation processing for estimated pulse wave information.

Here, the spectral entropy is an entropy calculated, regarding the power spectrum at each frequency of an input signal as a probability distribution. Specifically, if the value of the power spectrum of a frequency bin k obtained by Fourier transform of an input signal is $P_k$, the spectral entropy H with respect to the normalized $P_k$, that is, $p_k = P_k / \Sigma(P_k)$, is expressed by the following equation (1).

$$H = -\Sigma\{p_k \times \log_2(p_k)\} \quad (1)$$

This spectral entropy is a feature value representing the whiteness of the input signal. With a white noise with a uniform power spectrum, the spectral entropy has a high value. With a significant signal with an uneven power spectrum, the spectral entropy has a low value. The spectral entropy is independent of the signal intensity (amplitude).

In a phase where there is no body motion, if the pulse signal of high quality is acquired, the spectral entropy of the acceleration signal has a high value and the spectral entropy of the pulse signal has a low value.

If a body motion occurs and a leakage into the pulse signal is generated, the spectral entropy of the acceleration signal changes downward, whereas the spectral entropy of the pulse signal changes upward.

Particularly in a phase where the harmful influence of a body motion is noticeable in such a way that the pulse signal and the leakage are almost equal in strength, the spectrum of the pulse is more complex than the spectrum of the acceleration signal and consequently the spectral entropy of the pulse signal is higher than the spectral entropy of the acceleration signal.

Therefore, in this modification, the spectral entropy of the acceleration signal is compared with the spectral entropy of the pulse signal over every predetermined time range, and if the spectral entropy of the acceleration signal becomes lower than the spectral entropy of the pulse signal by more than a predetermined amount, the reliability of the pulse signal in this range is determined as low and the pulse signal with low reliability is not used for the estimation processing for estimated pulse wave information.

Figure 11:
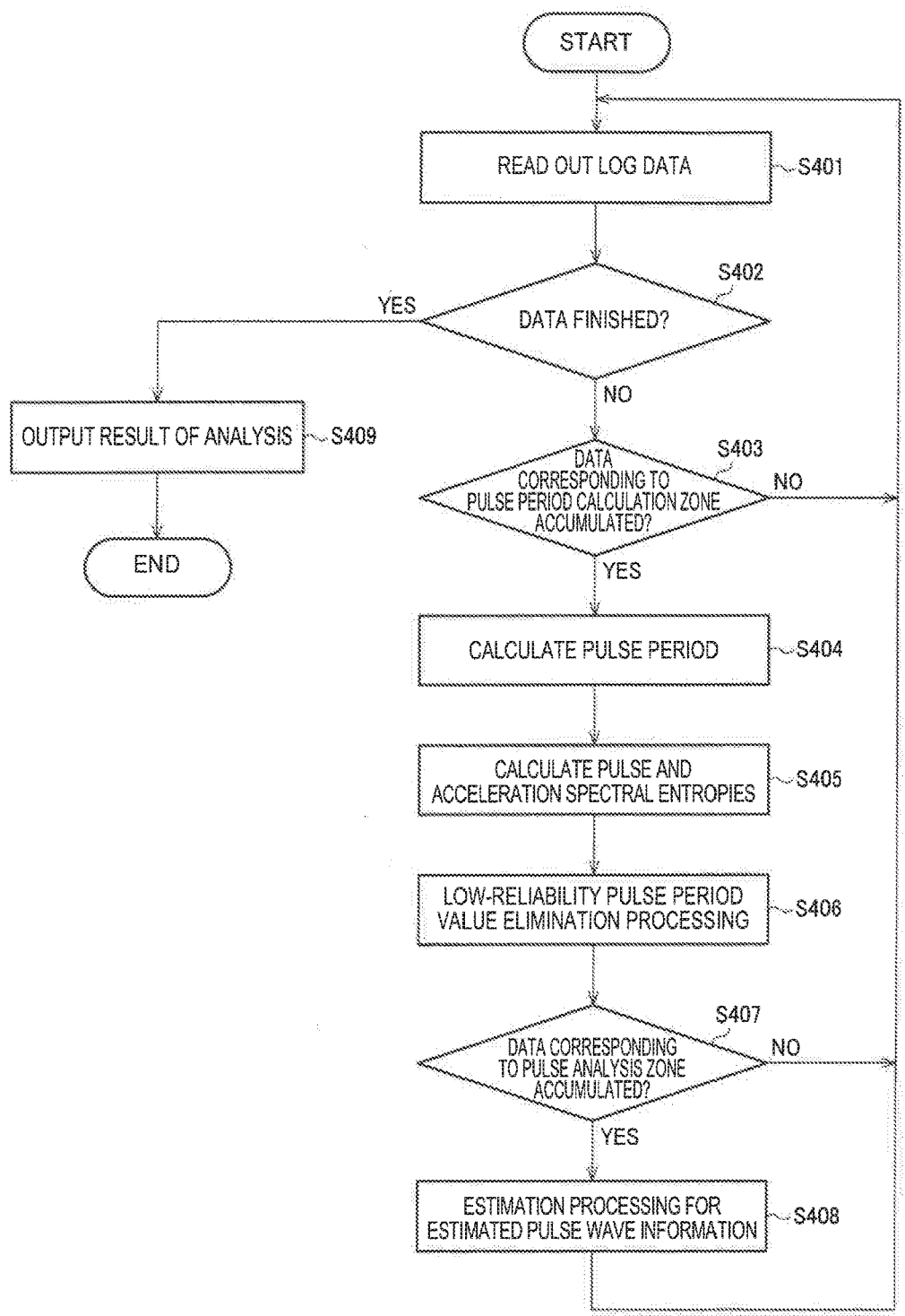
FIG. 11 is a flowchart for explaining a flow of reliability evaluation processing for pulse signal.

The flow of specific processing is shown in the flowchart of FIG. 11. The processing of Steps S401 to S407 in the flowchart of FIG. 11 is equivalent to the processing of Steps S101 and S108 in the flowchart of FIG. 8 or the like. The processing of Step S408 in FIG. 11 is equivalent to the processing of Steps S109 and S110 in FIG. 8.

First, the processing unit 110 reads out log data from a storage unit, not illustrated (S401). This log data includes a pulse signal (pulse wave sensor information) acquired from the pulse wave sensor 200 and an acceleration signal (body motion information) acquired from the acceleration sensor (body motion sensor 300) which are then stored in the storage unit, not illustrated.

The processing unit 110 then determines whether all the log data is read out from the storage unit or not (S402). If the processing unit 110 determines that not all the log data is read out (NO in S402), the processing unit 110 determines whether log data corresponding to a pulse period calculation zone is read out or not (S403). The pulse period calculation zone is a predetermined zone estimated to have a length equal to or longer than the pulse period of the user. If the processing unit 110 determines that the log data corresponding to the pulse period calculation zone is not read out (NO in S403), the processing unit 110 returns to Step S401.

Meanwhile, if the processing unit 110 determines that the log data corresponding to the pulse period calculation zone is read out (YES in S403), the processing unit 110 calculates the pulse period of the user from the log data thus read out (S404) and subsequently calculates the pulse spectral entropy based on the pulse signal and calculates the acceleration spectral entropy based on the acceleration signal (S405).

Next, the processing unit 110 performs low-reliability pulse period value elimination processing (S406). Specifically, as described above, the processing unit 110 compares the pulse spectral entropy with the acceleration spectral entropy, and if the spectral entropy of the acceleration signal becomes lower than the spectral entropy of the pulse signal by more than a predetermined amount, the processing unit 110 determines that the reliability of the pulse signal in this range is low, and decides not to use the pulse signal with low reliability for the estimation processing for estimated pulse wave information (S406).

After that, the processing unit 110 determines whether log data after Step S406, corresponding to a pulse analysis zone, is accumulated or not (S407). If the processing unit 110 determines that the log data corresponding to the pulse, analysis zone is accumulated (YES in S407), the processing unit 110 performs the estimation processing for estimated pulse wave information (S408). The pulse analysis zone is a predetermined zone such that estimated pulse wave information can be found using the log data acquired in that zone. Meanwhile, if the processing unit 110 determines that the log data corresponding to the pulse analysis zone is not accumulated (NO in S407), the processing unit 110 returns to Step S401.

If the processing unit 110 determines in Step S402 that all the log data is read out from the storage unit, the processing unit 110 outputs the result of analysis of Step S408 to the display unit or the storage unit, not illustrated, and ends the processing (S409).

As described above, in this modification, whether there is a harmful leakage of a body motion into the pulse signal or not can be determined more properly, by comparing the spectral entropies of the pulse signal and the acceleration signal. Therefore, according to this modification, the occurrence of problems such as invalidating a pulse signal which has no problems, or incorrectly analyzing a pulse signal in which a harmful leakage is generated due to large optical influence, can be improved and therefore more appropriate pulse analysis can be performed.

5. Specific Example of Wearable Device

Figure 12:
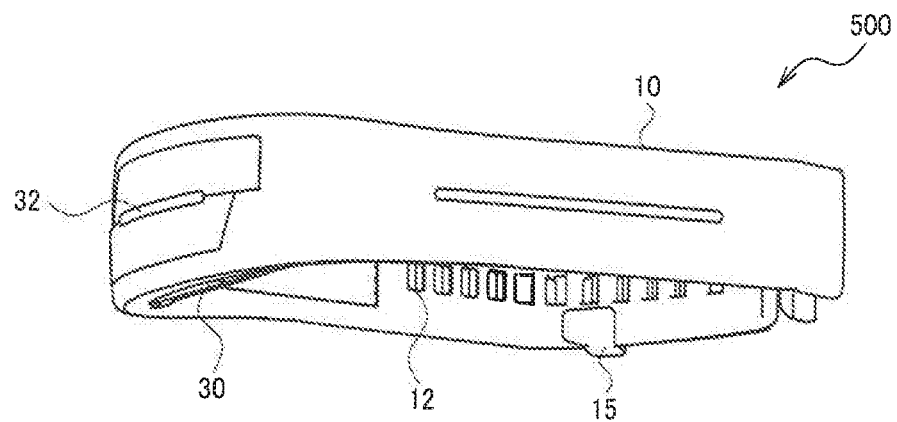
FIG. 12 shows an appearance of an electronic device.
Figure 13:
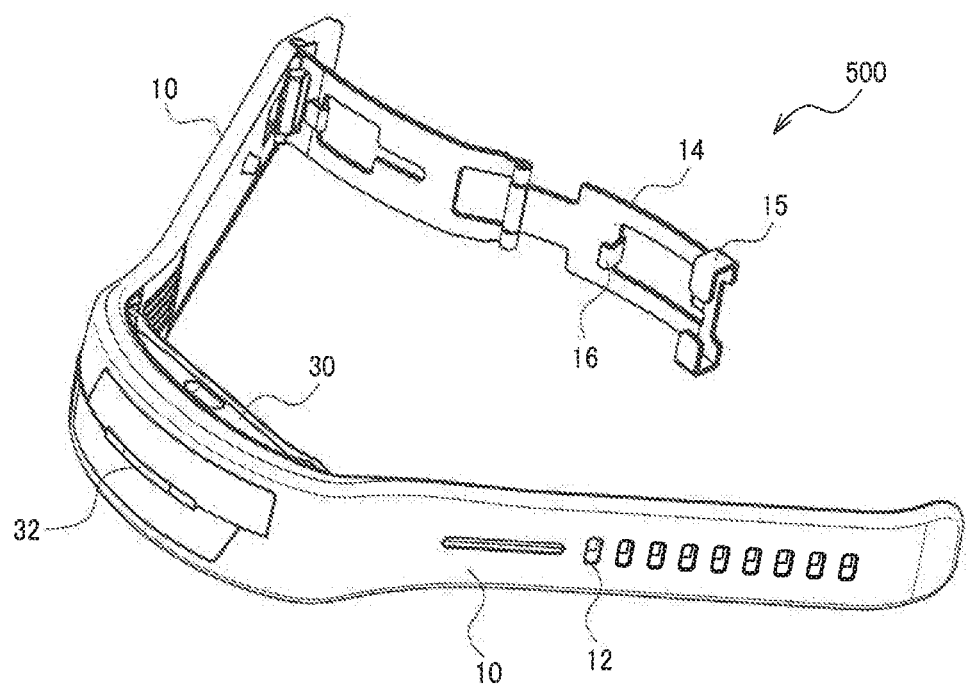
FIG. 13 shows another appearance of the electronic device.
Figure 14:
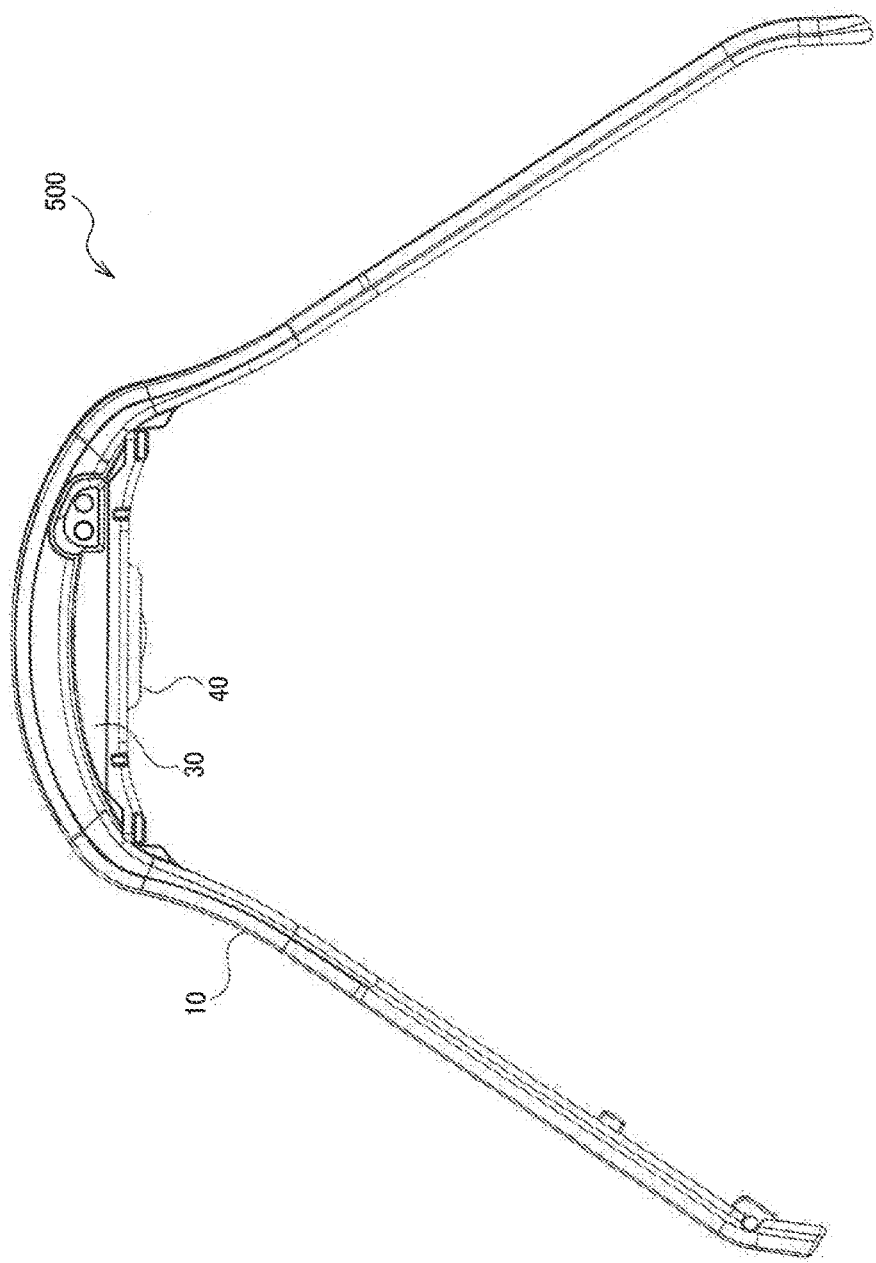
FIG. 14 shows still another appearance of the electronic device.

FIGS. 12 to 14 show an example of the appearance of the wearable device 500 acquiring biological information and body motion information. The wearable device 500 in this embodiment has a strap section 10, a case section 30, and a sensor section 40. As shown in FIGS. 12 and 13, the case section 30 is attached to the strap section 10. As shown in FIG. 14, the sensor section 40 is provided in the case section 30 and includes the pulse wave sensor 200 and the body motion sensor 300 described with reference to FIG. 1.

The strap section 10 is to be wound around the wrist of the user so that the user can wear the wearable device 500. The strap section 10 has a strap hole 12 and a buckle part 14. The buckle part 14 has a strap insertion part 15 and a protruding part 16. The user inserts one end of the strap section 10 into the strap insertion part 15 of the buckle part 14 and inserts the protruding part 16 of the buckle part 14 into the strap hole 12 of the strap section 10, thus wearing the wearable device 500 around the wrist. The strap section 10 may have a clasp instead of the buckle part 14.

The case section 30 is equivalent to the main body part of the wearable device 500. Inside the case section 30, various components of the wearable device 500 such as the sensor section 40 and a circuit board (processing unit 110) or the like, not illustrated are provided. That is, the case section 30 is a casing accommodating these components.

A light emitting window part 32 is provided in the case section 30. The light emitting window part 32 is formed of a light-transmitting member. A light emitting unit as an interface mounted on a flexible substrate is provided in the case section 30, and the light from the light emitting unit is emitted out of the case section 30 via the light emitting window part 32. Also, in the case section 30, a display unit such as an LCD (liquid crystal display) may be provided instead of the light emitting unit, or the display unit and the light emitting unit may be provided together.

Figure 15:
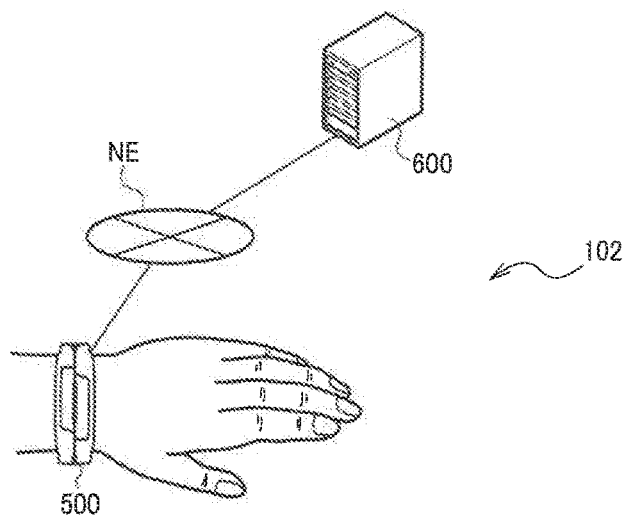
FIG. 15 is an explanatory view of a biological information processing system.

The wearable device 500 is worn around the wrist of the user, as shown in FIG. 15 or the like. In this wearing state, biological information and body motion information are measured.

The wearable device 500 in the embodiment is not limited to the example shown in FIGS. 12 to 14. For example, the wearable device 500 may be a chest belt-type wearable electrocardiograph, not illustrated.

6. Specific Example of Implementation of Biological Information Processing System Next, a specific example of a device which implements the biological information processing system 102 according to the embodiment will be described. The functions of the biological information processing system 102 may be implemented by the wearable device 500 (electronic device) and the server system 600, for example, as shown in FIG. 15. In this case, the wearable device 500 (electronic device) includes the pulse wave sensor 200 and the body motion sensor 300. The server system 600 includes the processing unit 110. An example of this case is FIG. 15. For example, the server system 600 is connected to the wearable device 500 (electronic device) via a network NE and acquires pulse wave sensor information and body motion information of the subject from this wearable device 500. Since the wearable device 500 worn by the user needs to be small-sized and lightweight, the processing capability of the battery and the processing unit inside the device, or the data storage capacity is greatly limited. Meanwhile, the server system 600 has less limitation to its resources and therefore can carry out, for example, the processing of estimating estimated pulse wave information based on body motion information at a high speed and can hold more data.

Figure 16:
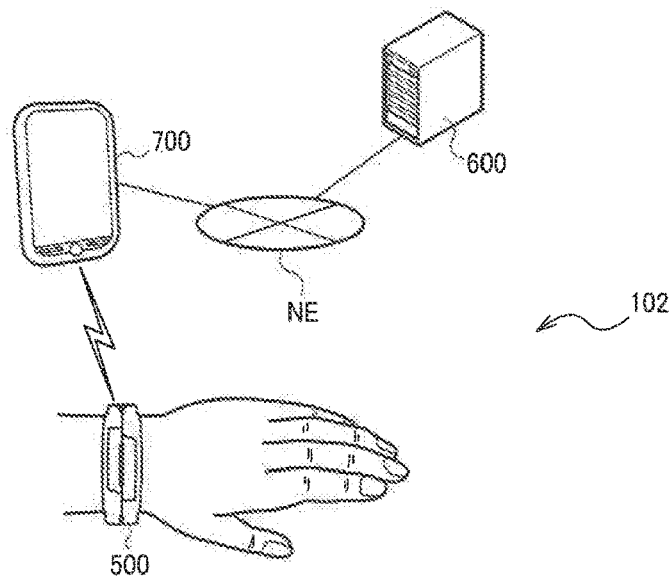
FIG. 16 is another explanatory view of the biological information processing system.

It suffices that the server system 600 can acquire various types of information collected by the wearable device 500. Therefore, the server system 600 is not limited to being directly connected to the wearable device 500. For example, as shown in FIG. 16, the wearable device 500 may be connected to another processing device 700, and the server system 600 may be connected to the processing device 700 via a network NE. The processing device 700 in this case may be a portable terminal device such as a smartphone used by the user wearing the wearable device 500, for example. For the connection between the wearable device 500 and the processing device 700, a communication measure similar to the network NE may be used. However, short-range wireless communication or the like can be used as well.

Figure 17:
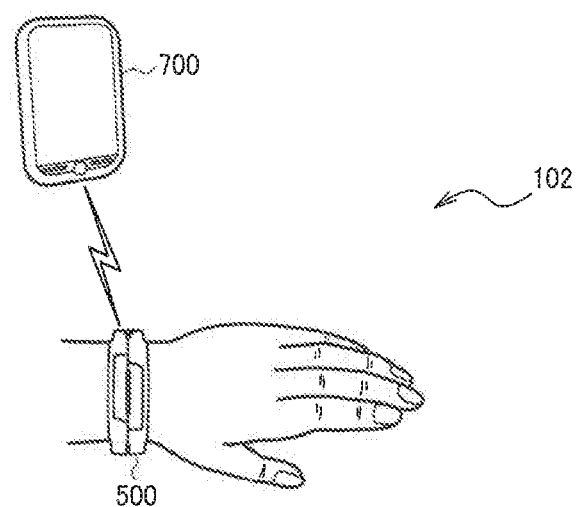
FIG. 17 is still another explanatory view of the biological information processing system.

The biological information processing system 102 according to the embodiment may also be implemented by the processing device 700 (electronic device; in a narrow sense, portable terminal device) such as a smartphone, and the wearable device 500, instead of the server system 600, as shown in FIG. 17. The portable terminal device such as a smartphone often has more limitations to the processing capability, storage area and battery capacity than the server system 600. However, given the recent improvement in capabilities, the portable terminal device may be able to secure sufficient processing capability. Therefore, if the requirement of processing capability or the like is satisfied, a smartphone or the like can be used as the biological information processing system 102 according to the embodiment, as shown in FIG. 17.

Moreover, when the improvement in the capabilities or the use of the terminal is considered, a form of embodiment in which the wearable device 500 (electronic device) includes the biological information processing system 102 according to the above embodiment above may be employed. In this case, the processing unit 110 acquires information from the pulse wave sensor 200 and the body motion sensor 300 provided inside the same device. In the case where the biological information processing system 102 is installed in the wearable device 500, the biological information processing system 102 is less likely to need to perform data analysis, saving or the like for a large number of users, and may only have to target one or a small number of users using the wearable device 500. That is, it is very likely that even the processing capability of the wearable device 500 can satisfy the needs of the user.

That, is, the method in the embodiment can be applied to a terminal device (biological information processing device, biological information analysis device, biological information measuring device, biological information detection device) including a processing unit which estimates estimated pulse wave information of a user, based on body motion information of the user that is acquired.

Also, in the biological information processing system 102, for example, the processing of acquiring body motion information and the estimation processing for estimated pulse wave information may be implemented by distributed processing by a plurality of devices. Specifically, the biological information processing system 102 may be implemented by at least two or more of the server system 600, the processing device 700, and the wearable device 500, as in the examples shown in FIGS. 15 and 16. Alternatively, another device may perform a part of the processing by the biological information processing system 102. The biological information processing system 102 according to the embodiment can be implemented by various devices (or combinations of devices). Alternatively, the biological information processing system 102 may be implemented by a single device.

In the biological information processing system and the electronic device or the like according to the embodiment, a part or most of the processing may be implemented by a program. In this case, a processor such as a CPU executes the program, thus implementing the biological information processing system and the electronic device or the like according to the embodiment. Specifically, the program stored in a non-temporary information storage device is read out, and the processor such as a CPU executes the read-out program. Here, the information storage device (computer-readable device) stores a program, data and the like. The functions of the information storage device can be implemented by an optical disk (DVD, CD or the like), HDD (hard disk drive), or memory (memory card, ROM or the like). The processor such as a CPU carries cat various kinds of processing in the embodiment, based on the program (data) stored in the information storage device. That is, a program which causes a computer (device having an operation unit, a processing unit, a storage unit, and an output unit) to function as each component of the embodiment (program for causing a computer to execute the processing by each component) is stored in the information storage device.

Thus, the processing in the embodiment can be implemented by a program. The program may be, for example, a program read out and executed by the processing unit of a device like a smartphone (for example, DSP).

Although the embodiment has been described in detail above, a person skilled in the art can readily understand that various modifications can be made without substantially departing from the new matters and advantageous effects of the invention. Therefore, all such modifications are included in the scope of the invention. For example, a term described along with a different term with a broader meaning or the same meaning at least once in the specification or drawings can be replaced with the different term at any point in the specification or drawings. Also, the configurations and operations of the biological information processing device and the program are not limited to those described in the embodiment and can be carried out with various modifications.

What is claimed is:

1. A biological information processing device comprising:
   a pulse wave sensor which measures a pulse wave of a user;
   a body motion sensor which detects a body motion of the user; and
   a processing unit which performs estimation processing for pulse wave information of the user,
   wherein the processing unit performs intermittent on/off control in which the pulse wave sensor is intermittently switched on/off, and the processing unit performs the estimation processing based on body motion information acquired using a signal from the body motion sensor during an off-period of the pulse wave sensor, and
   wherein the pulse wave sensor is off under the intermittent on/off control in at least one situation selected from the group of:
   i) no electricity is supplied to the pulse wave sensor;
   ii) an electricity consumption by the pulse wave sensor is smaller than at the time of measurement; and
   iii) no pulse signal is output from the pulse wave sensor.

2. The biological information processing device according to claim 1,
   wherein the processing unit
   specifies exercise state information indicating an exercise state of the user based on the body motion information, and
   performs the estimation processing for the pulse wave information based on corresponding relationship information between the exercise state information and the pulse wave information of the user, and the exercise state information.

3. The biological information processing device according to claim 2, further comprising
   a detection unit which detects at least one user action, of attachment of the biological information processing device to the user, a movement of the user, and an input operation by the user,
   wherein the processing unit starts the estimation processing if the user action is detected by the detection unit.

4. The biological information processing device according to claim 2,
   wherein the processing unit switches on an operation of the pulse wave sensor after the estimation processing is started.

5. The biological information processing device according to claim 3,
   wherein the processing unit
   finds reference pulse wave information of the user by the estimation processing, and
   performs the estimation processing, based on pulse wave sensor information acquired from the pulse wave sensor whose operation is on, and the reference pulse wave information.

6. The biological information processing device according to claim 1, further comprising
   a detection unit which detects at least one user action, of attachment of the biological information processing device to the user, a movement of the user, and an input operation by the user,
   wherein the processing unit starts the estimation processing if the user action is detected by the detection unit.

7. The biological information processing device according to claim 6,
   wherein the processing unit switches on an operation of the pulse wave sensor after the estimation processing is started.

8. The biological information processing device according to claim 1,
   wherein the processing unit switches on an operation of the pulse wave sensor after the estimation processing is started.

9. The biological information processing device according to claim 1,
   wherein the processing unit starts the estimation processing at a timing before a timing when the operation of the pulse wave sensor is switched on from off.

10. The biological information processing device according to claim 1,
    wherein if it is determined that an estimated value of pulse rate found by the estimation processing is in an unchanged state, the processing unit stops the estimation processing until it is determined that the estimated value of pulse rate is in a changed state.

11. The biological information processing device according to claim 10,
    wherein the processing unit uses the pulse wave information acquired when the estimation processing is stopped, as an initial value, when resuming the estimation processing after the estimation processing is stopped.

12. The biological information processing device according to claim 1,
    wherein the processing unit
    performs determination processing in which an exercise state of the user is determined based on the body motion information,
    stops the estimation processing if it is determined that the exercise state is in an unchanged state from the time of the previous determination processing, and resumes the estimation processing if it is determined that the exercise state of the user is in a changed state.

13. The biological information processing device according to claim 1,
wherein the processing unit performs processing in which at least one item of information from among exercise intensity, target exercise intensity and calories burned, of the user, is specified based on the pulse wave information estimated by the estimation processing, when the operation of the pulse wave sensor is off.

14. A biological information processing device causing a computer to function as a processing unit configured to acquire pulse wave sensor information from a pulse wave sensor which measures a pulse wave of a user, acquire body motion information using a signal from a body motion sensor which detects a body motion of the user, and perform estimation processing for pulse wave information of the user, by a program recorded in a computer-readable recording medium,
wherein the processing unit performs intermittent on/off control in which the pulse wave sensor is intermittently switched on/off, and the processing unit performs the estimation processing based on the body motion information during an off-period of the pulse wave sensor, and
wherein the pulse wave sensor is off under the intermittent on/off control in at least one situation selected from the group of:
i) no electricity is supplied to the pulse wave sensor;
ii) an electricity consumption by the pulse wave sensor is smaller than at the time of measurement; and
iii) no pulse signal is output from the pulse wave sensor.

15. The biological information processing device according to claim 14,
wherein the processing unit switches on an operation of the pulse wave sensor after the estimation processing is started.

16. The biological information processing device according to claim 14,
wherein the processing unit performs processing in which at least one item of information from among exercise intensity, target exercise intensity and calories burned, of the user, is specified based on the pulse wave information estimated by the estimation processing, when the operation of the pulse wave sensor is off.

17. The biological information processing device according to claim 14,
wherein the processing unit
specifies exercise state information indicating an exercise state of the user based on the body motion information, and
performs the estimation processing for the pulse wave information based on corresponding relationship information between the exercise state information and the pulse wave information of the user, and the exercise state information.

18. A biological information processing method comprising:
measuring a pulse wave of a user with a pulse wave sensor;
detecting a body motion of the user with a body motion sensor; and
performing estimation processing for pulse wave information of the user,
wherein intermittent on/off control in which the pulse wave sensor is intermittently switched on/off is performed, and the estimation processing is performed based on body motion information acquired using a signal from the body motion sensor during an off-period of the pulse wave sensor, and
wherein the pulse wave sensor is off under the intermittent on/off control in at least one situation selected from the group of:
i) no electricity is supplied to the pulse wave sensor;
ii) an electricity consumption by the pulse wave sensor is smaller than at the time of measurement; and
iii) no pulse signal is output from the pulse wave sensor.

19. The biological information processing method according to claim 18,
wherein an operation of the pulse wave sensor is switched on after the estimation processing is started.

20. The biological information processing method according to claim 18,
wherein exercise state information indicating an exercise state of the user is specified based on the body motion information, and
the estimation processing for the pulse wave information is performed based on corresponding relationship information between the exercise state information and the pulse wave information of the user, and the exercise state information.

* * * * *